United States Patent
Wu et al.

(10) Patent No.: US 12,259,373 B2
(45) Date of Patent: Mar. 25, 2025

(54) HIGH CONFIDENCE COMPOUND IDENTIFICATION BY LIQUID CHROMATOGRAPHY-MASS SPECTROMETRY

(71) Applicant: Regeneron Pharmaceuticals, Inc., Tarrytown, NY (US)

(72) Inventors: Jikang Wu, Chappaqua, NY (US); Hongxia Wang, Briarcliff Manor, NY (US); Haibo Qiu, Hartsdale, NY (US); Ning Li, New Canaan, CT (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 18/610,673

(22) Filed: Mar. 20, 2024

(65) Prior Publication Data

US 2024/0230604 A1 Jul. 11, 2024

Related U.S. Application Data

(63) Continuation of application No. 17/828,858, filed on May 31, 2022, now Pat. No. 11,959,897, which is a continuation of application No. 17/162,648, filed on Jan. 29, 2021, now Pat. No. 11,371,971.

(60) Provisional application No. 62/968,525, filed on Jan. 31, 2020.

(51) Int. Cl.
*G01N 30/72* (2006.01)
*G01N 30/86* (2006.01)
(Continued)

(52) U.S. Cl.
CPC ..... *G01N 30/7233* (2013.01); *G01N 30/8644* (2013.01); *H01J 49/0031* (2013.01);
(Continued)

(58) Field of Classification Search
CPC .......... G01N 30/8644; G01N 30/7233; G01N 30/8679; G01N 2030/628; G01N 33/6848;
(Continued)

(56) References Cited

U.S. PATENT DOCUMENTS 9,134,318 B2   9/2015   Madian et al.
9,283,287 B2   3/2016   Chakraborty et al.
(Continued)

FOREIGN PATENT DOCUMENTS

EP   1740954 B1   8/2015
WO   2004/090933 A2   10/2004

OTHER PUBLICATIONS

Rubin et al., "Measurement of Inositol Trisphosphate by Gas Chromatography/Mass Spectrometry: Femtomole Sensitivity Provided by Negative-Ion Chemical Ionization Mass Spectrometry in Submilligram Quantities of Tissue," Methods in Neurosciences, vol. 18:201-212, (1993).

(Continued)

*Primary Examiner* — Kiet T Nguyen
(74) *Attorney, Agent, or Firm* — Schwabe, Williamson & Wyatt P.C.; David Mellman (57) ABSTRACT

Disclosed are methods for improving compound detection and characterization. Methods for characterizing a sample are disclosed. The methods can include providing a sample to a liquid chromatography system capable of sample separation to generate sample components; analyzing sample components by multiplexed targeted selected ion monitoring (SIM) to generate an inclusion list; and performing iterative mass spectral data-dependent acquisition (DDA) from the inclusion list, to identify individual sample components thereby characterizing the sample. In one example, multiplexed targeted SIMs and iterative MS2 DDA acquisition is used to increase robust compound identification for cell culture medium analysis.

20 Claims, 8 Drawing Sheets

(51) Int. Cl.
  *H01J 49/00* (2006.01)
  *H01J 49/04* (2006.01)
  *H01J 49/42* (2006.01)
  *G01N 30/62* (2006.01)

(52) U.S. Cl.
  CPC ........ *H01J 49/0431* (2013.01); *H01J 49/425* (2013.01); *G01N 2030/628* (2013.01)

(58) Field of Classification Search
  CPC .. H01J 49/0031; H01J 49/0431; H01J 49/425; H01J 49/4225
  USPC .......................................................... 250/282
  See application file for complete search history.

(56) References Cited

U.S. PATENT DOCUMENTS

| | | |
|---|---|---|
| 9,897,581 B1 | 2/2018 | Prakash et al. |
| 11,371,971 B2 | 6/2022 | Wu et al. |
| 11,959,897 B2 | 4/2024 | Wu et al. |
| 2013/0224855 A1 | 8/2013 | Gupta et al. |
| 2015/0194296 A1* | 7/2015 | Verenchikov ....... H01J 49/0027 250/282 |
| 2020/0095316 A1 | 3/2020 | Stanimirovic et al. |
| 2020/0393465 A1 | 12/2020 | Greene et al. |
| 2021/0225627 A1 | 7/2021 | Xuan |

OTHER PUBLICATIONS

Sleeman et al., "Selected Ion Monitoring," Mass Spectrometry, pp. 423-430, (2005).
U.S. Appl. No. 17/162,648, Notice of Allowance mailed Mar. 1, 2022.
U.S. Appl. No. 17/828,858, Non-Final Office Action mailed Mar. 16, 2023.
U.S. Appl. No. 17/828,858, Final Office Action mailed Sep. 8, 2023.
U.S. Appl. No. 17/828,858, Notice of Allowance mailed Dec. 21, 2023.
WIPO Application No. PCT/US2021/015806, PCT International Search Report and Written Opinion of the International Searching Authority mailed May 28, 2021.

* cited by examiner

Detection of stable isotope labeled compounds spiked at different concentration in soy hydrolysate

| Stable isotope labeled compound | Concentration | | | | |
|---|---|---|---|---|---|
| | 1μM | 0.1μM | 0.01μM | 0.001μM | 0.0001μM |
| Glycine | Both | Both | Both | Both | Both |
| Alanine | Both | ND | ND | ND | ND |
| Serine | Both | Both | Only in SIM | ND | ND |
| Proline | Both | Only in SIM | Only in SIM | ND | ND |
| Valine | Both | ND | ND | ND | ND |
| Threonine | Both | Both | ND | ND | ND |
| nicotinamide | Both | ND | ND | ND | ND |
| nicotinate | Both | Only in SIM | ND | ND | ND |
| N-Acetyl-alanine | Both | Both | Both | Both | Both |
| Asparagine | Both | Both | Only in SIM | ND | ND |
| Aspartic acid | Both | Both | Both | ND | ND |
| Ornithine | Both | ND | ND | ND | ND |
| Leucine | Both | Both | Only in SIM | ND | ND |
| Isoleucine | Both | Both | Both | ND | ND |
| Glutamine | Both | Both | Both | ND | ND |
| Glutamic acid | Both | Both | ND | ND | ND |
| Lysine | Both | Both | ND | ND | ND |
| Methionine | Both | Both | Both | ND | ND |
| Histidine | Both | Both | ND | ND | ND |
| Phenylalanine | Both | Both | ND | ND | ND |
| Arginine | Both | Only in SIM | ND | ND | ND |
| Tyrosine | Both | Both | Only in FS | ND | ND |
| Tryptophan | Both | Both | Both | Both | Both |
| Cystine | Both | Both | Both | ND | ND |
| 5'-Methylthioadenosine | Both | Both | Both | ND | ND |
| HEPES D16 | Both | Both | ND | ND | ND |
| Vitamin B12 2+ | Both | Only in SIM | Only in SIM | Only in SIM | Only in SIM |
| Folate (Vitamin B9) 2+ | Both | Only in SIM | ND | ND | ND |

Only in SIM: only detected with targeted SIMs
Only in FS: only detected with full scan
Both: detected with both acquisition methods
ND: not detected with either acquisition method

HIGH CONFIDENCE COMPOUND IDENTIFICATION BY LIQUID CHROMATOGRAPHY-MASS SPECTROMETRY

CROSS-REFERENCE TO RELATED APPLICATIONS

This application is a continuation of U.S. application Ser. No. 17/828,858, filed May 31, 2022, which is a continuation of U.S. application Ser. No. 17/162,648, filed Jan. 29, 2021, now U.S. Pat. No. 11,371,971, which claims the benefit under 35 USC § 119(e) of U.S. Provisional Application No. 62/968,525, filed Jan. 31, 2020, each of which is incorporated herein by reference in its entirety for all purposes.

FIELD OF THE INVENTION

The present invention pertains to compound identification, and in particular, to a method for high confidence compound identification by liquid chromatography-mass spectrometry (LC-MS), such as for antibody process development.

BACKGROUND

Cell culture medium plays a key role in antibody production. It is highly desirable and challenging to develop a deeper understanding of how individual components and their metabolites within the cell culture medium impact the production performance. Despite the shift of using chemically defined medium, soy-based medium is still widely used. The major components and impurities of soy hydrolysates have been shown to affect antibodies' productivity and quality. Mass spectrometry plays important roles in compound quantification and identification in highly complex matrices. Liquid chromatography-mass spectrometry (LC-MS)-based analysis could benefit tremendously from improved data quality, which can subsequently lead to improved characterization with higher confidence and less ambiguity.

BRIEF SUMMARY OF THE INVENTION

In one aspect, the present invention provides a method of characterizing a sample, comprising: providing the sample to a liquid chromatography system capable of sample separation to generate sample components; analyzing sample components by multiplexed targeted selected ion monitoring (SIM) to generate an inclusion list; and performing iterative mass spectral data-dependent acquisition (DDA) from the inclusion list, to identify individual sample components thereby characterizing the sample.

In some embodiments, the liquid chromatography system is a reversed phase liquid chromatography (RPLC) system.

In some embodiments, analyzing the ionized sample by multiplexed targeted selected ion monitoring (SIM) to generate an inclusion list comprises utilizing an ion trap or orbitrap mass analyzer.

In some embodiments, performing iterative mass spectral data-dependent acquisition (DDA) comprises utilizing an ion trap or orbitrap mass analyzer fitted with a segmented quadrupole mass filter.

In some embodiments, analyzing sample components by multiplexed targeted selected ion monitoring (SIM) to generate an inclusion list comprises segmenting mass to ratio window settings in which multiple segments are included and each segment has multiple windows.

In some embodiments, multiple segments is three segments.

In some embodiments, multiple segments is four segments.

In some embodiments, multiple windows is 10 windows.

In some embodiments, each window within a segment has the same window width.

In some embodiments, the sample is cell culture medium.

In some embodiments, the cell culture medium is a soy-based cell culture medium.

In some embodiments, the cell culture medium is for a recombinant cell-based production system.

In some embodiments, the method is for characterizing components and their metabolites within the cell culture medium following incubation with a recombinant cell-based production system.

In some embodiments, the recombinant cell-based production system is a mammalian system.

In some embodiments, the recombinant cell-based production system is for protein production.

In some embodiments, the protein is an antibody, a fusion protein, recombinant protein, or a combination thereof.

In some embodiments, the antibody is a monoclonal antibody.

In some embodiments, the monoclonal antibody is of isotype IgG1, IgG2, IgG3, IgG4, or mixed isotype.

Also disclosed is a method of compound identification for cell culture medium analysis, comprising: providing the sample of cell culture medium to a liquid chromatography system capable of sample separation to generate sample components; analyzing sample components by multiplexed targeted selected ion monitoring (SIM) to generate an inclusion list; and performing iterative mass spectral data-dependent acquisition (DDA) from the inclusion list, to identify individual compounds with the cell culture medium.

In some embodiments, the liquid chromatography system is a reversed phase liquid chromatography (RPLC) system.

In some embodiments, analyzing the fragmented sample by multiplexed targeted selected ion monitoring (SIM) to generate an inclusion list comprises utilizing an ion trap or orbitrap mass analyzer.

In some embodiments, performing iterative mass spectral data-dependent acquisition (DDA) comprises utilizing an ion trap or orbitrap mass analyzer fitted with a segmented quadrupole mass filter.

In some embodiments, analyzing sample components by multiplexed targeted selected ion monitoring (SIM) to generate an inclusion list comprises segmenting mass to ratio window settings in which multiple segments are included and each segment has multiple windows.

In some embodiments, multiple segments is three segments.

In some embodiments, multiple segments is four segments.

In some embodiments, multiple windows is 10 windows.

In some embodiments, each window within a segment has the same window width.

In some embodiments, the cell culture medium is a soy-based cell culture medium.

In some embodiments, the cell culture medium is for a recombinant cell-based production system.

In some embodiments, the cell culture medium sample is a cell culture medium sample obtained following incubation with a recombinant cell-based production system.

In some embodiments, the recombinant cell-based production system is a mammalian system.

In some embodiments, the recombinant cell-based production system is for protein production.

In some embodiments, the protein is an antibody, a fusion protein, recombinant protein, or a combination thereof.

In some embodiments, the antibody is a monoclonal antibody.

In some embodiments, the monoclonal antibody is of isotype IgG1, IgG2, IgG3, IgG4, or mixed isotype.

In various embodiments, any of the features or components of embodiments discussed above or herein may be combined, and such combinations are encompassed within the scope of the present disclosure. Any specific value discussed above or herein may be combined with another related value discussed above or herein to recite a range with the values representing the upper and lower ends of the range, and such ranges and all values falling within such ranges are encompassed within the scope of the present disclosure. Each of the values discussed above or herein may be expressed with a variation of 1%, 5%, 10% or 20%. Other embodiments will become apparent from a review of the ensuing detailed description.

DETAILED DESCRIPTION OF THE INVENTION

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims. Any embodiments or features of embodiments can be combined with one another, and such combinations are expressly encompassed within the scope of the present invention.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

As used herein, the terms "include," "includes," and "including," are meant to be non-limiting and are understood to mean "comprise," "comprises," and "comprising," respectively.

Although any methods and materials similar or equivalent to those described herein can be used in the practice or testing of the present invention, the preferred methods and materials are now described. All patents, applications and non-patent publications mentioned in this specification are incorporated herein by reference in their entireties.

Abbreviations Used Herein

ACN: Acetonitrile
CHO: Chinese Hamster Ovary
CQA: Critical Quality Attributes
CV: Coefficient of Variations
DDA: Data-Dependent Acquisition
EIC: Extracted Ion Chromatograph
ESI-MS: Electrospray Ionization Mass Spectrometry
FA: Formic Acid
HC: Heavy Chain
HILIC: Hydrophilic Interaction Liquid Chromatography
HMW: High Molecular Weight
IgG: Immunoglobulin G
IPA: Isopropanol
LC: Light Chain
LC-MS: Liquid Chromatography-Mass Spectrometry
LMW: Low Molecular Weight
mAb: Monoclonal Antibody
MS: Mass Spectrometry
MW: Molecular Weight
M/Z: Mass-to-Charge Ratio
NCE: Normalized Collision Energy
PK: Pharmacokinetics
PQA: Product Quality Attribute
PTM: Post-translational Modification
RP-LC: Reversed Phase Liquid Chromatography
SIM: Selected Ion Monitoring Definitions As used herein, the term "protein" includes any amino acid polymer having covalently linked amide bonds. Proteins comprise one or more amino acid polymer chains, generally known in the art as "polypeptides." "Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. "Synthetic peptides or polypeptides' refers to a non-naturally occurring peptide or polypeptide. Synthetic peptides or polypeptides can be synthesized, for example, using an automated polypeptide synthesizer. Various solid phase peptide synthesis methods are known to those of skill in the art. A protein may contain one or multiple polypeptides to form a single functioning biomolecule. A protein can include any of bio-therapeutic proteins, recombinant proteins used in research or therapy, trap proteins and other chimeric receptor Fc-fusion proteins, chimeric proteins, antibodies, monoclonal antibodies, polyclonal antibodies, human antibodies, and bispecific antibodies. In another exemplary aspect, a protein can include antibody fragments, nanobodies, recombinant antibody chimeras, cytokines, chemokines, peptide hormones, and the like. Proteins may be produced using recombinant cell-based production systems, such as the insect bacculovirus system, yeast systems (e.g., *Pichia* sp.), mammalian systems (e.g., CHO cells and CHO derivatives like CHO-K1 cells). For a recent review discussing biotherapeutic proteins and their production, see Ghaderi et al., "Production platforms for biotherapeutic glycoproteins. Occurrence, impact, and challenges of non-human sialylation," (Biotechnol. Genet. Eng. Rev. (2012) 147-75). In some embodiments, proteins comprise modifications, adducts, and other covalently linked moieties. Those modifications, adducts and moieties include for example avidin, streptavidin, biotin, glycans (e.g., N-acetylgalactosamine, galactose, neuraminic acid, N-acetylglucosamine, fucose, mannose, and other monosaccharides), PEG, polyhistidine, FLAGtag, maltose binding protein (MBP), chitin binding protein (CBP), glutathione-S-transferase (GST) myc-epitope, fluorescent labels and other dyes, and the like. Proteins can be classified on the basis of compositions and solubility and can thus include simple proteins, such as, globular proteins and fibrous proteins; conjugated proteins, such as, nucleoproteins, glycoproteins, mucoproteins, chromoproteins, phosphoproteins, metalloproteins, and lipoproteins; and derived proteins, such as, primary derived proteins and secondary derived proteins.

Variant protein" or "protein variant", or "variant" as used herein can include a protein that differs from a target protein by virtue of at least one amino acid modification. Protein variant may refer to the protein itself, a composition comprising the protein, or the amino sequence that encodes it. Preferably, the protein variant has at least one amino acid modification compared to the parent protein, e.g. from about one to about ten amino acid modifications, and preferably from about one to about five amino acid modifications compared to the parent. The protein variant sequence herein will preferably possess at least about 80% homology with a parent protein sequence, and most preferably at least about 90% homology, more preferably at least about 95% homology. In some exemplary embodiments, the protein can be an antibody, a bispecific antibody, a multispecific antibody, antibody fragment, monoclonal antibody, or combinations thereof.

The term "antibody", as used herein, is intended to refer to immunoglobulin molecules comprised of four polypeptide chains, two heavy (H) chains and two light (L) chains inter-connected by disulfide bonds (i.e., "full antibody molecules"), as well as multimers thereof (e.g. IgM) or antigen-binding fragments thereof. Each heavy chain is comprised of a heavy chain variable region ("HCVR" or "$V_H$") and a heavy chain constant region (comprised of domains $C_H1$, $C_H2$ and $C_H3$). In various embodiments, the heavy chain may be an IgG isotype. In some cases, the heavy chain is selected from IgG1, IgG2, IgG3 or IgG4. In some embodiments, the heavy chain is of isotype IgG1 or IgG4, optionally including a chimeric hinge region of isotype IgG1/IgG2 or IgG4/IgG2. Each light chain is comprised of a light chain variable region ("LCVR or "$V_L$") and a light chain constant region ($C_L$). The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The term "antibody" includes reference to both glycosylated and non-glycosylated immunoglobulins of any isotype or subclass. The term "antibody" includes antibody molecules prepared, expressed, created or isolated by recombinant means, such as antibodies isolated from a host cell transfected to express the antibody. For a review on antibody structure, see Lefranc et al., *IMGT unique numbering for immunoglobulin and T cell receptor variable domains and Ig superfamily V-like domains,* 27(1) Dev. Comp. Immunol. 55-77 (2003); and M. Potter, *Structural correlates of immunoglobulin diversity,* 2(1) Surv. Immunol. Res. 27-42 (1983).

The term antibody also encompasses "bispecific antibody", which includes a heterotetrameric immunoglobulin that can bind to more than one different epitope. One half of the bispecific antibody, which includes a single heavy chain and a single light chain and six CDRs, binds to one antigen or epitope, and the other half of the antibody binds to a different antigen or epitope. In some cases, the bispecific antibody can bind the same antigen, but at different epitopes or non-overlapping epitopes. In some cases, both halves of the bispecific antibody have identical light chains while retaining dual specificity. Bispecific antibodies are described generally in U.S. Patent App. Pub. No. 2010/0331527 (Dec. 30, 2010).

The term "antigen-binding portion" of an antibody (or "antibody fragment"), refers to one or more fragments of an antibody that retain the ability to specifically bind to an antigen. Examples of binding fragments encompassed within the term "antigen-binding portion" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al. (1989) Nature 241:544-546), which consists of a VH domain, (vi) an isolated CDR, and (vii) an scFv, which consists of the two domains of the Fv fragment, VL and VH, joined by a synthetic linker to form a single protein chain in which the VL and VH regions pair to form monovalent molecules. Other forms of single chain antibodies, such as diabodies are also encompassed under the term "antibody" (see e.g., Holliger et al. (1993) 90 PNAS U.S.A. 6444-6448; and Poljak et al. (1994) 2 Structure 1121-1123).

Moreover, antibodies and antigen-binding fragments thereof can be obtained using standard recombinant DNA techniques commonly known in the art (see Sambrook et al., 1989). Methods for generating human antibodies in transgenic mice are also known in the art. For example, using VELOCIMMUNE® technology (see, for example, U.S. Pat. No. 6,596,541, Regeneron Pharmaceuticals, VELOCIMMUNE®) or any other known method for generating monoclonal antibodies, high affinity chimeric antibodies to a desired antigen are initially isolated having a human variable region and a mouse constant region. The VELOCIMMUNE® technology involves generation of a transgenic mouse having a genome comprising human heavy and light chain variable regions operably linked to endogenous mouse constant region loci such that the mouse produces an antibody comprising a human variable region and a mouse constant region in response to antigenic stimulation. The DNA encoding the variable regions of the heavy and light chains of the antibody are isolated and operably linked to DNA encoding the human heavy and light chain constant regions. The DNA is then expressed in a cell capable of expressing the fully human antibody The term "human antibody", is intended to include antibodies having variable and constant regions derived from human germline immunoglobulin sequences. The human mAbs of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include mAbs in which CDR sequences derived from the germline of another mammalian species (e.g., mouse), have been grafted onto human FR sequences. The term includes antibodies recombinantly produced in a non-human mammal, or in cells of a non-human mammal. The term is not intended to include antibodies isolated from or generated in a human subject.

As used herein, the term "subject" refers to an animal, preferably a mammal, more preferably a human, for example in need of amelioration, prevention and/or treatment of a disease or disorder.

As used herein, the term "impurity" can include any undesirable protein present in the biopharmaceutical product. Impurity can include process and product-related impurities. The impurity can further be of known structure, partially characterized, or unidentified. Process-related impurities can be derived from the manufacturing process and can include the three major categories: cell substrate-derived, cell culture-derived and downstream derived. Cell substrate-derived impurities include, but are not limited to, proteins derived from the host organism and nucleic acid (host cell genomic, vector, or total DNA). Cell culture-derived impurities include, but are not limited to, inducers, antibiotics, serum, and other media components. Downstream-derived impurities include, but are not limited to, enzymes, chemical and biochemical processing reagents (e.g., cyanogen bromide, guanidine, oxidizing and reducing agents), inorganic salts (e.g., heavy metals, arsenic, nonmetallic ion), solvents, carriers, ligands (e.g., monoclonal antibodies), and other leachables. Product-related impurities (e.g., precursors, certain degradation products) can be molecular variants arising during manufacture and/or storage that do not have properties comparable to those of the desired product with respect to activity, efficacy, and safety. Such variants may need considerable effort in isolation and characterization in order to identify the type of modification(s). Product-related impurities can include truncated forms, modified forms, and aggregates. Truncated forms are formed by hydrolytic enzymes or chemicals which catalyze the cleavage of peptide bonds. Modified forms include, but are not limited to, deamidated, isomerized, mismatched S—S linked, oxidized, or altered conjugated forms (e.g., glycosylation, phosphorylation). Modified forms can also include any post-translational modification form. Aggregates include dimers and higher multiples of the desired product (Q6B Specifications: Test Procedures and Acceptance Criteria for Biotechnological/Biological Products, ICH August 1999, U.S. Dept. of Health and Humans Services).

The term "low molecular weight (LMW) protein drug impurity" includes but is not limited to precursors, degradation products, truncated species, proteolytic fragments including Fab fragments, Fc or heavy chain fragments, ligand or receptor fragments, H2L (2 heavy chains and 1 light chain), H2 (2 heavy chains), HL (1 heavy chain and 1 light chain), HC (1 heavy chain), and LC (1 light chain) species. A LMW protein drug impurity can be any variant which is an incomplete version of the protein product, such as one or more components of a multimeric protein. Protein drug impurity, drug impurity or product impurity are terms that may be used interchangeably throughout the specification. LMW drug or product impurities are generally considered molecular variants with properties such as activity, efficacy, and safety that may be different from those of the desired drug product.

Degradation of protein product is problematic during production of the protein drug product in cell culture systems. For example, proteolysis of a protein product may occur due to release of proteases in cell culture medium. Medium additives, such as soluble iron sources added to inhibit metalloproteases, or serine and cysteine proteases inhibitors, have been implemented in cell culture to prevent degradation (Clincke, M.-F., et al, BMC Proc. 2011, 5, P115). C-terminal fragments may be cleaved during production due to carboxyl peptidases in the cell culture (Dick, L W et al, Biotechnol Bioeng 2008; 100:1132-43).

The term "high molecular weight (HMW) protein drug impurity" includes but is not limited to mAb trimers and mAb dimers. HMW species can be divided into two groups: 1) monomer with extra light chains (H2L3 and H2L4 species) and 2) monomer plus Fab fragments complexes. In addition, after treatment with IdeS enzymatic digestion, different dimerized fragments (Fab2-Fab2, Fc-Fc and Fab2-Fc) are formed.

A "post-translational modification" (PTM) refers to the covalent modification of proteins following protein biosynthesis. Post-translational modifications can occur on the amino acid side chains or at the protein's C- or N-termini. PTMs are generally introduced by specific enzymes or enzyme pathways. Many occur at the site of a specific characteristic protein sequence (e.g., signature sequence) within the protein backbone. Several hundred PTMs have been recorded, and these modifications invariably influence some aspect of a protein's structure or function (Walsh, G. "Proteins" (2014) second edition, published by Wiley and Sons, Ltd., ISBN: 9780470669853). The various post-translational modifications include, but are not limited to, cleavage, N-terminal extensions, protein degradation, acylation of the N-terminus, biotinylation (acylation of lysine residues with a biotin), amidation of the C-terminal, glycosylation, iodination, covalent attachment of prosthetic groups, acetylation (the addition of an acetyl group, usually at the N-terminus of the protein), alkylation (the addition of an alkyl group (e.g. methyl, ethyl, propyl) usually at lysine or arginine residues), methylation, adenylation, ADP-ribosylation, covalent cross links within, or between, polypeptide chains, sulfonation, prenylation, Vitamin C dependent modifications (proline and lysine hydroxylations and carboxy terminal amidation), Vitamin K dependent modification wherein Vitamin K is a cofactor in the carboxylation of glutamic acid residues resulting in the formation of a γ-carboxyglutamate (a glu residue), glutamylation (covalent linkage of glutamic acid residues), glycylation (covalent linkage glycine residues), glycosylation (addition of a glycosyl group to either asparagine, hydroxylysine, serine, or threonine, resulting in a glycoprotein), isoprenylation (addition of an isoprenoid group such as farnesol and geranylgeraniol), lipoylation (attachment of a lipoate functionality), phosphopantetheinylation (addition of a 4'-phosphopantetheinyl moiety from coenzyme A, as in fatty acid, polyketide, non-ribosomal peptide and leucine biosynthesis), phosphorylation (addition of a phosphate group, usually to serine, tyrosine, threonine or histidine), and sulfation (addition of a sulfate group, usually to a tyrosine residue). The post-translational modifications that change the chemical nature of amino acids include, but are not limited to, citrullination (e.g., the conversion of arginine to citrulline by deimination), and deamidation (e.g., the conversion of glutamine to glutamic acid or asparagine to aspartic acid). The post-translational modifications that involve structural changes include, but are not limited to, formation of disulfide bridges (covalent linkage of two cysteine amino acids) and proteolytic cleavage (cleavage of a protein at a peptide bond). Certain post-translational modifications involve the addition of other proteins or peptides, such as ISGylation (covalent linkage to the ISG15 protein (Interferon-Stimulated Gene)), SUMOylation (covalent linkage to the SUMO protein (Small Ubiquitin-related MOdifier)) and ubiquitination (covalent linkage to the protein ubiquitin). See www.uniprot.org/docs/ptmlist for a more detailed controlled vocabulary of PTMs curated by UniProt.

The term as used herein, "glycopeptide/glycoprotein" is a modified peptide/protein, during or after their synthesis, with covalently bonded carbohydrates or glycan. In certain embodiments, a glycopeptide is obtained from a monoclonal antibody, for example, from a protease digest of a monoclonal antibody.

The term as used herein, "glycan" is a compound comprising one or more of sugar units which commonly include glucose (Glc), galactose (Gal), mannose (Man), fucose (Fuc), N-acetylgalactosamine (GalNAc), N-acetylglucosamine (GlcNAc) and N-acetylneuraminic acid (NeuNAc) (Frank Kjeldsen, et al. Anal. Chem. 2003, 75, 2355-2361). The glycan moiety in glycoprotein, such as a monoclonal antibody, is an important character to identify its function or cellular location. For example, a specific monoclonal antibody is modified with specific glycan moiety.

The term "sample," as used herein, refers to a mixture of molecules such components within cell culture medium that is subjected to manipulation in accordance with the methods of the invention, including, for example, separating, analyzing, or profiling. A sample can comprise at least an analyte molecule, e.g., glycopeptide, such as obtained from a monoclonal antibody, that is subjected to manipulation in accordance with the methods of the invention, including, for example, separating, analyzing, extracting, concentrating or profiling.

The terms "analysis" or "analyzing," as used herein, are used interchangeably and refer to any of the various methods of separating, detecting, isolating, purifying, solubilizing, detecting and/or characterizing molecules of interest. Examples include, but are not limited to, solid phase extraction, solid phase micro extraction, electrophoresis, mass spectrometry, e.g., Multiplexed targeted selected ion monitoring (SIM)-MS followed by iterative MS2 DDA, ESI-MS, SPE HILIC, or MALDI-MS, liquid chromatography, e.g., high performance, e.g., reverse phase, normal phase, or size exclusion, ion-pair liquid chromatography, liquid-liquid extraction, e.g., accelerated fluid extraction, supercritical fluid extraction, microwave-assisted extraction, membrane extraction, soxhlet extraction, precipitation, clarification, electrochemical detection, staining, elemental analysis, Edmund degradation, nuclear magnetic resonance, infrared analysis, flow injection analysis, capillary electrochromatography, ultraviolet detection, and combinations thereof.

The term "profiling," as used herein, refers to any of various methods of analysis which are used in combination to provide the content, composition, or characteristic ratio of compounds, such as proteins.

"Contacting," as used herein, includes bringing together at least two substances in solution or solid phase.

"Peptide mapping analysis" as used herein includes experiments wherein the protein undergoes digestion followed by separation of the resulting peptides and their analysis, preferably using LC-MS. In some exemplary embodiments, peptide mapping analysis can be applied to confirm the primary sequence of protein biopharmaceuticals, where a protein molecule can be first hydrolyzed into small peptide fragments using a hydrolyzing agent and then the amino acid sequence of each peptide fragment is determined by LC-MS analysis taking into consideration of the cDNA predicted sequence and the specificity of the protease used. Data from peptide mapping analysis could also be utilized to identify and quantify post-translational modifications, confirm the disulfide bond linkages and even detect amino acid substitution events present at very low levels (<0.1%) (Zeck et al. PloS one 2012, 7, e40328). During peptide mapping analysis of protein biopharmaceuticals, LC-MS can be often performed in combination with ultraviolet (UV) detection to generate so-called UV fingerprints, which alone can be used as an identification assay during quality control (QC) and drug release.

As used herein, the term "digestion" refers to hydrolysis of one or more peptide bonds of a protein. There are several approaches to carrying out digestion of a protein in a sample using an appropriate hydrolyzing agent, for example, enzymatic digestion or non-enzymatic digestion. As used herein, the term "hydrolyzing agent" refers to any one or combination of a large number of different agents that can perform digestion of a protein. Non-limiting examples of hydrolyzing agents that can carry out enzymatic digestion include trypsin, endoproteinase Arg-C, endoproteinase Asp-N, endoproteinase Glu-C, outer membrane protease T (OmpT), immunoglobulin-degrading enzyme of Streptococcus pyogenes (IdeS), chymotrypsin, pepsin, thermolysin, papain, pronase, and protease from Aspergillus Saitoi. Non-limiting examples of hydrolyzing agents that can carry out non-enzymatic digestion include the use of high temperature, microwave, ultrasound, high pressure, infrared, solvents (non-limiting examples are ethanol and acetonitrile), immobilized enzyme digestion (IMER), magnetic particle immobilized enzymes, and on-chip immobilized enzymes. For a recent review discussing the available techniques for protein digestion see Switazar et al., "Protein Digestion: An Overview of the Available Techniques and Recent Developments" (J. Proteome Research 2013, 12, 1067-1077). One or a combination of hydrolyzing agents can cleave peptide bonds in a protein or polypeptide, in a sequence-specific manner, generating a predictable collection of shorter peptides.

Several approaches are available that can be used to digest a protein. One of the widely accepted methods for digestion of proteins in a sample involves the use of proteases. Many proteases are available and each of them has their own characteristics in terms of specificity, efficiency, and optimum digestion conditions. Proteases refer to both endopeptidases and exopeptidases, as classified based on the ability of the protease to cleave at non-terminal or terminal amino acids within a peptide. Alternatively, proteases also refer to the six distinct classes—aspartic, glutamic, and metalloproteases, cysteine, serine, and threonine proteases, as classified on the mechanism of catalysis. The terms "protease" and "peptidase" are used interchangeably to refer to enzymes which hydrolyze peptide bonds. Proteases can also be classified into specific and non-specific proteases. As used herein, the term "specific protease" refers to a protease with an ability to cleave the peptide substrate at a specific amino acid side chain of a peptide. As used herein, the term "non-specific protease" refers to a protease with a reduced ability to cleave the peptide substrate at a specific amino acid side chain of a peptide. A cleavage preference may be determined based on the ratio of the number of a particular amino acid as the site of cleavage to the total number of cleaved amino acids in the protein sequences.

The protein can optionally be prepared before characterizing. In some exemplary embodiments, the protein preparation includes a step of protein digestion. In some specific exemplary embodiments, the protein preparation includes a step of protein digestion, wherein the protein digestion can be carried out using trypsin.

In some exemplary embodiments, the protein preparation can include a step for denaturing the protein, reducing the protein, buffering the protein, and/or desalting the sample, before the step of protein digestion. These steps can be accomplished in any suitable manner as desired.

To provide characterization of different protein attributes using either peptide mapping analysis or intact mass analysis, a wide variety of LC-MS based assays can be performed.

As used herein, the term "liquid chromatography" refers to a process in which a chemical mixture carried by a liquid can be separated into components as a result of differential distribution of the chemical entities as they flow around or over a stationary liquid or solid phase. Non-limiting examples of liquid chromatography include reverse phase liquid chromatography, ion-exchange chromatography, size exclusion chromatography, affinity chromatography, and hydrophobic chromatography.

As used herein, the term "mass spectrometer" refers to a device capable of detecting specific molecular species and accurately measuring their masses. The term can be meant to include any molecular detector into which a polypeptide or peptide may be eluted for detection and/or characterization. A mass spectrometer consists of three major parts: the ion source, the mass analyzer, and the detector. The role of the ion source is to create gas phase ions. Analyte atoms, molecules, or clusters can be transferred into gas phase and ionized either concurrently (as in electrospray ionization). The choice of ion source depends on the application.

As used herein, "mass analyzer" refers to a device that can separate species, that is, atoms, molecules, or clusters, according to their mass. Non-limiting examples of mass analyzers that could be employed are time-of-flight (TOF), magnetic/electric sector, quadrupole mass filter (Q), quadrupole ion trap (QIT), orbitrap, Fourier transform ion cyclotron resonance (FTICR), and also the technique of accelerator mass spectrometry (AMS).

As used herein, "mass-to-charge ratio" or "m/z" is used to denote the dimensionless quantity formed by dividing the mass of an ion in unified atomic mass units by its charge number (regardless of sign). In general, the charge state depends on: the method of ionization (as electrospray ionization, ESI tends to promote multiple ionization, which is not as frequent in MALDI), peptide length (as longer peptides have more groups where additional protons can be attached (basic residues)), peptide sequence (as some amino acids (e.g., Arg or Lys) are more susceptible to ionization than others), the instrument settings, solvent pH, and solvent composition.

As used herein, the term "tandem mass spectrometry" refers to a technique where structural information on sample molecules can be obtained by using multiple stages of mass selection and mass separation. A prerequisite is that the sample molecules can be transferred into gas phase and ionized intact and that they can be induced to fall apart in some predictable and controllable fashion after the first mass selection step. Multistage MS/MS, or MSn, can be performed by first selecting and isolating a precursor ion (MS2), fragmenting it, isolating a primary fragment ion (MS3), fragmenting it, isolating a secondary fragment (MS4), and so on as long as one can obtain meaningful information or the fragment ion signal is detectable. Tandem MS have been successfully performed with a wide variety of analyzer combinations. What analyzers to combine for a certain application can be determined by many different factors, such as sensitivity, selectivity, and speed, but also size, cost, and availability. The two major categories of tandem MS methods are tandem-in-space and tandem-in-time, but there are also hybrids where tandem-in-time analyzers are coupled in space or with tandem-in-space analyzers.

A tandem-in-space mass spectrometer comprise of an ion source, a precursor ion activation device, and at least two non-trapping mass analyzers. Specific m/z separation functions can be designed so that in one section of the instrument ions are selected, dissociated in an intermediate region, and the product ions are then transmitted to another analyzer for m/z separation and data acquisition.

In tandem-in-time mass spectrometer ions produced in the ion source can be trapped, isolated, fragmented, and m/z separated in the same physical device.

"Targeted mass spectrometry," as used herein, is a mass spectrometry technique that uses multiple stages of tandem mass spectrometry (MSn with n=2 or 3) for ions of specific mass (m/z), at specific time. The values of the m/z and time are defined in an inclusion list which is derived from a previous analysis.

As used herein, the term "quadrupole-Orbitrap hybrid mass spectrometer" refers to a hybrid system made by coupling a quadrupole mass spectrometer to an orbitrap mass analyzer. A tandem in-time experiment using the quadrupole-Orbitrap hybrid mass spectrometer begins with ejection of all ions except those within a selected, narrow m/z range from the quadrupole mass spectrometer. The selected ions can be inserted into orbitrap and fragmented most often by low-energy CID. Fragments within the m/z acceptance range of the trap should remain in the trap, and an MS-MS spectrum can be obtained. Similar hybrid systems can be used for fast protein sequencing, such as, but not limited to QIT-FTICR and Qq-FTICR.

As used herein, the term "protein de novo sequencing" refers to a procedure for determination of the amino acid sequence of a peptide without relying on the information gained from other sources. Due to the high level of sensitivity of mass spectrometry, this technique can provide vital information that is often beyond the capabilities of conventional sequencing methods.

As used herein, the term "protein sequence coverage" refers to the percentage of the protein sequence covered by identified peptides. The percent coverage can be calculated by dividing the number of amino acids in all found peptides by the total number of amino acids in the entire protein sequence.

As used herein, the term "database" refers to bioinformatic tools which provide the possibility of searching the uninterpreted MS-MS spectra against all possible sequences in the database(s). Non-limiting examples of such tools are Mascot (www.matrixscience.com), Spectrum Mill (www.chem.agilent.com), PLGS (www.waters.com), PEAKS (www.bioinformaticsolutions.com), Proteinpilot (download.appliedbiosystems.com//proteinpilot), Phenyx (www.phenyx-ms.com), Sorcerer (www.sagenresearch.com), OMSSA (www.pubchem.ncbi.nlm.nih.gov/omssa/), X!Tandem (www.thegpm.org/TANDEM/), Protein Prospector (www.prospector.ucsf.edu/prospector/mshome.htm), Byonic (www.proteinmetrics.com/products/byonic) or Sequest (fields.scripps.edu/sequest).

General Description

From the foregoing it will be appreciated that a need exists for improved methods and systems to improve compound detection and characterization. The disclosed invention meets that need. Disclosed herein are methods for high confidence compound identification by liquid chromatography-mass spectrometry (LC-MC), such as for antibody process development. Embodiments disclosed herein provide methods for robust, highly sensitivity sample characterization by combining multiplexed targeted SIMs and iterative MS2 DDA acquisition.

In some exemplary embodiments, the method includes providing a sample to a liquid chromatography system capable of sample separation to generate sample components; analyzing sample components by multiplexed targeted selected ion monitoring (SIM) to generate an inclusion list; and performing iterative mass spectral data-dependent acquisition (DDA) from the inclusion list, to identify individual sample components thereby characterizing the sample.

In some embodiments, providing the sample to a liquid chromatography system capable of sample separation to generate sample components comprises providing the sample to a reverse phase liquid chromatography (RPLC) system, ion-exchange chromatography system, size exclusion chromatography system, affinity chromatography system, hydrophilic-interaction chromatography system, or hydrophobic chromatography system.

In some embodiments, the liquid chromatography system is a RPLC system. In some particular embodiments, RPLC analysis is performed using a Supelco Discovery HS F5-3 column. The column temperature can be maintained at a constant temperature throughout the chromatography run, e.g., using a commercial column heater. In some embodiments, the column is maintained at a temperature between about 18° C. to about 70° C., e.g., about 30° C. to about 60° C., about 40° C. to about 50° C., e.g., at about 20° C., about 25° C., about 30° C., about 35° C., about 40° C., about 45° C., about 50° C., about 55° C., about 60° C., about 65° C., or about 70° C. In some embodiments, the column temperature is about 40° C. In some embodiments, the run time can be between about 15 to about 240 minutes, e.g., about 20 to about 70 min, about 30 to about 60 min, about 40 to about 90 min, about 50 min to about 100 min, about 60 to about 120 min, about 50 to about 80 min.

In some embodiments, the mobile phase is an aqueous mobile phase. A representative aqueous mobile phase contains 140 mM sodium acetate and 10 mM ammonium bicarbonate. The UV traces are typically recorded at 215 and 280 nm.

In some exemplary embodiments, the mobile phase used to elute the protein can be a mobile phase that can be compatible with a mass spectrometer.

In some exemplary embodiments, the mobile phase used in the liquid chromatography device can include water, acetonitrile, trifluoroacetic acid, formic acid, or combination thereof.

In some exemplary embodiments, the mobile phase can have a flow rate of about 0.1 ml/min to about 0.4 ml/min in the liquid chromatography device. In one aspect, the flow rate of the mobile phase in the liquid chromatography device can be about 0.1 ml/min, about 0.15 ml/min, about 0.20 ml/min, about 0.25 ml/min, about 0.30 ml/min, about 0.35 ml/min, or about 0.4 ml/min.

In some embodiments, analyzing sample components by multiplexed targeted selected ion monitoring (SIM) to generate an inclusion list comprises utilizing an ion trap or orbitrap mass analyzer. In some embodiments, the ion trap or orbitrap mass analyzer is a Thermo Q Exactive HF Orbitrap mass spectrometer.

In some embodiments, analyzing sample components by multiplexed targeted selected ion monitoring (SIM) to generate an inclusion list comprises segmenting mass to ratio window settings in which multiple segments are included and each segment has multiple windows. In some embodiments, at least two, at least three, at least four, at least five or more segments are used. In some embodiments, three segments are used. In some embodiments, four segments are used.

In some embodiments, each segment includes multiple windows of the same width. In some embodiments, at least 2 or more windows are used, such as at least 3, at least 4, at least 5, at least 6, at least 7, at least 8, at least 9, at least 10 windows are used. In some embodiments, each segment includes 10 windows.

Figure 2:
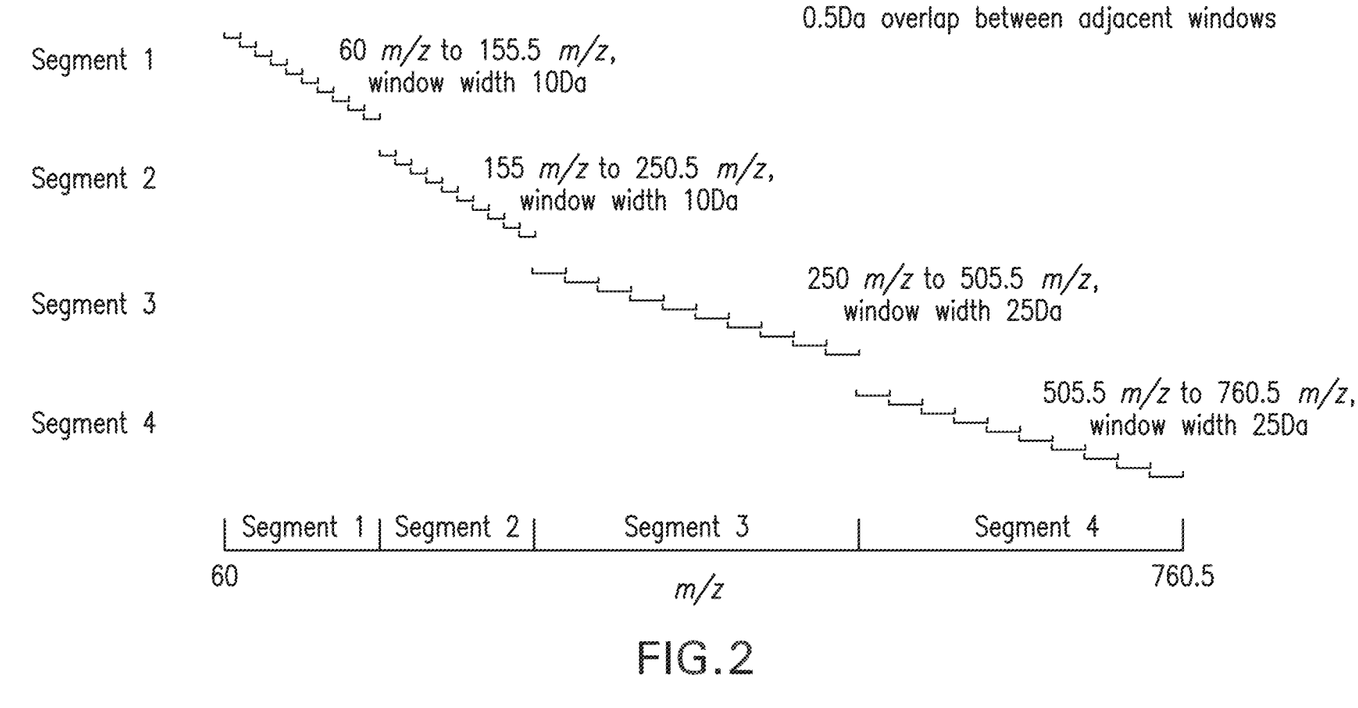
FIG. 2 shows a schematic illustrating an exemplary adjustable window selection protocol.

In some embodiments, window width varies amongst the multiple segments. For example, the window width in ranges of m/z of most interest are more narrow than those of less interest. In some embodiments, the segments one and two have window widths of a narrower width than segments three and four. For example, as shown in FIG. 2, an exemplary regiment can include four segments ranging from 60 to 760.5 m/z: Segment 1, 60 m/z to 155.5 m/z with a window width of 10 Da; Segment 2, 155 m/z to 250.5 m/z, window width 10 Da; Segment 3, 250 m/z to 505.5 m/z, window width 25 DA; and Segment 4, 505.5 m/z to 760.5 m/z, window width 25 Da wherein each segment includes 10 windows and 0.5 Da overlap between adjacent windows.

In embodiments, following generation of an inclusion list the method includes performing iterative MS2 DDA from the inclusion list to identify individual sample components thereby characterizing the sample.

In some exemplary embodiments, iterative MS DDA utilizes an ion trap or orbitrap mass analyzer fitted with a segmented quadrupole mass filter.

In some exemplary embodiments, iterative MS DDA utilizes a commercially available ion trap or orbitrap mass analyzer fitted with a segmented quadrupole mass filter, such as a Thermo Orbitrap™ Fusion Lumos mass spectrometer.

In some exemplary embodiments, data is processed following iterative MS DDA, such as by use of In some embodiments, the sample is cell culture medium, such as cell culture medium used in fed-batch cell culture, continuous cell culture or perfusion cell culture.

In some embodiments, the sample cell culture medium is a soy-based cell culture medium.

In some exemplary embodiments, the cell culture medium is for a recombinant cell-based production system, such as a mammalian system. In some embodiments, In some embodiments, the method is for characterizing components and their metabolites within the cell culture medium prior or following incubation with a recombinant cell-based production system. In some embodiments, the recombinant cell-based production system is for protein production. Exemplary proteins include, but are not limited to, an antibody, a fusion protein, recombinant protein, or a combination thereof.

In some embodiments, the antibody is a bispecific antibody, antibody fragment or a multispecific antibody.

In some exemplary embodiments, the antibody is a monoclonal antibody, such as, but not limited to, a monoclonal antibody of isotype IgG1, IgG2, IgG3, IgG4, or mixed isotype.

In some exemplary embodiments, the protein is be a therapeutic protein.

In some exemplary embodiments, the protein can be an immunoglobulin protein.

In one exemplary embodiment, the protein can be a protein variant.

In one exemplary embodiment, the protein can be a post-translationally modified protein.

In one exemplary embodiment, the post-translationally modified protein can be a formed by cleavage, N-terminal extensions, protein degradation, acylation of the N-terminus, biotinylation, amidation of the C-terminal, oxidation, glycosylation, iodination, covalent attachment of prosthetic groups, acetylation, alkylation, methylation, adenylation, ADP-ribosylation, covalent cross links within, or between, polypeptide chains, sulfonation, prenylation, Vitamin C dependent modifications, Vitamin K dependent modification, glutamylation, glycylation, glycosylation, deglycosylation, isoprenylation, lipoylation, phosphopantetheinylation, phosphorylation, sulfation, citrullination, deamidation, formation of disulfide bridges, proteolytic cleavage, ISGylation, SUMOylation or ubiquitination (covalent linkage to the protein ubiquitin).

In one exemplary embodiment, the post-translationally modified protein can be formed on oxidation of a protein.

In another exemplary embodiment, the cell culture medium can include a degradation product, such as a post-translation modification of a therapeutic protein.

In some exemplary embodiments, the protein can be a protein with a pI in the range of about 4.5 to about 9.0. In one aspect, the protein can be a protein with a pI of about 4.5, about 5.0, about 5.5, about 5.6, about 5.7, about 5.8, about 5.9, about 6.0, about 6.1 about 6.2, about 6.3, about 6.4, about 6.5, about 6.6, about 6.7, about 6.8, about 6.9, about 7.0, about 7.1 about 7.2, about 7.3, about 7.4, about 7.5, about 7.6, about 7.7, about 7.8, about 7.9, about 8.0, about 8.1 about 8.2, about 8.3, about 8.4, about 8.5, about 8.6, about 8.7, about 8.8, about 8.9, or about 9.0.

In some embodiments, the identified components include, but are not limited to, amino acids, dipeptides, tripeptides, or a combination thereof with an abundance dynamic range of at least 2 orders of magnitude, such as at least 3 orders of magnitude, at least 4 orders of magnitude or greater. In some embodiments, the identified components include one or more of the compounds provided in FIG. 7.

In some exemplary embodiments, one or more compounds/components detected can include one or more product-related impurities. Exemplary product related impurities can be, but are not limited to, molecular variants, precursors, degradation products, fragmented protein, digested product, aggregates, post-translational modification form or combinations thereof.

In some specific exemplary embodiments, the one or more compounds/components detected can be a process-related impurity. The process-related impurity can include impurities derived from the manufacturing process, e.g., nucleic acids and host cell proteins, antibiotics, serum, other media components, enzymes, chemical and biochemical processing reagents, inorganic salts, solvents, carriers, ligands, and other leachables used in the manufacturing process that may be present or released into the cell culture medium.

In some embodiments, the disclosed method is a method of compound identification for cell culture medium analysis, comprising: providing the sample of cell culture medium to a liquid chromatography system capable of sample separation to generate sample components; analyzing sample components by multiplexed targeted selected ion monitoring (SIM) to generate an inclusion list; and performing iterative mass spectral data-dependent acquisition (DDA) from the inclusion list, to identify individual compounds within the cell culture medium. In some examples, the method further includes culturing cells producing a recombinant protein, such as antibody, for example in cell culture medium, obtaining a sample from the cell culture at a desired time point prior to characterizing the cell culture medium components.

In some embodiments, the method includes identifying cell culture medium components by the using the disclosed method followed by modifying one or more culture conditions of the cell culture to reduce the amount of characterized compound produced during cell culture of the protein. Exemplary conditions of the cell culture that can be changed include, but are not limited to, temperature, pH, cell density, amino acid concentration, osmolality, growth factor concentration, agitation, gas partial pressure, surfactants, or combinations thereof.

In some embodiments, the cells producing the protein, such as the antibody, are CHO cells. In other embodiments, the cells are hybridoma cells.

EXAMPLES

The following examples are put forth so as to provide those of ordinary skill in the art with a complete disclosure and description of how to make and use the methods of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, room temperature is about 25° C., and pressure is at or near atmospheric.

Example 1: Materials and Methods

Pooled soy hydrolysates were dissolved in Milli-Q water as the matrix. Stable isotope labeled compound standards were spiked in with final concentration ranging from several nanomolar to hundreds of millimolar. A Supelco Discovery HS F5-3 column was used for reversed-phase liquid chromatography (RPLC) separation. Multiplexed targeted selected ion monitoring (SIM) was performed on a Thermo Q Exactive HF Orbitrap mass spectrometer to generate the inclusion list. Iterative MS2 data-dependent acquisition (DDA) from inclusion list was conducted on a Thermo Orbitrap Fusion Lumos mass spectrometer. MS1 full scan followed by conventional MS2 DDA was performed as comparison. Compound Discoverer 3.1 was used for data processing.

Figure 1:
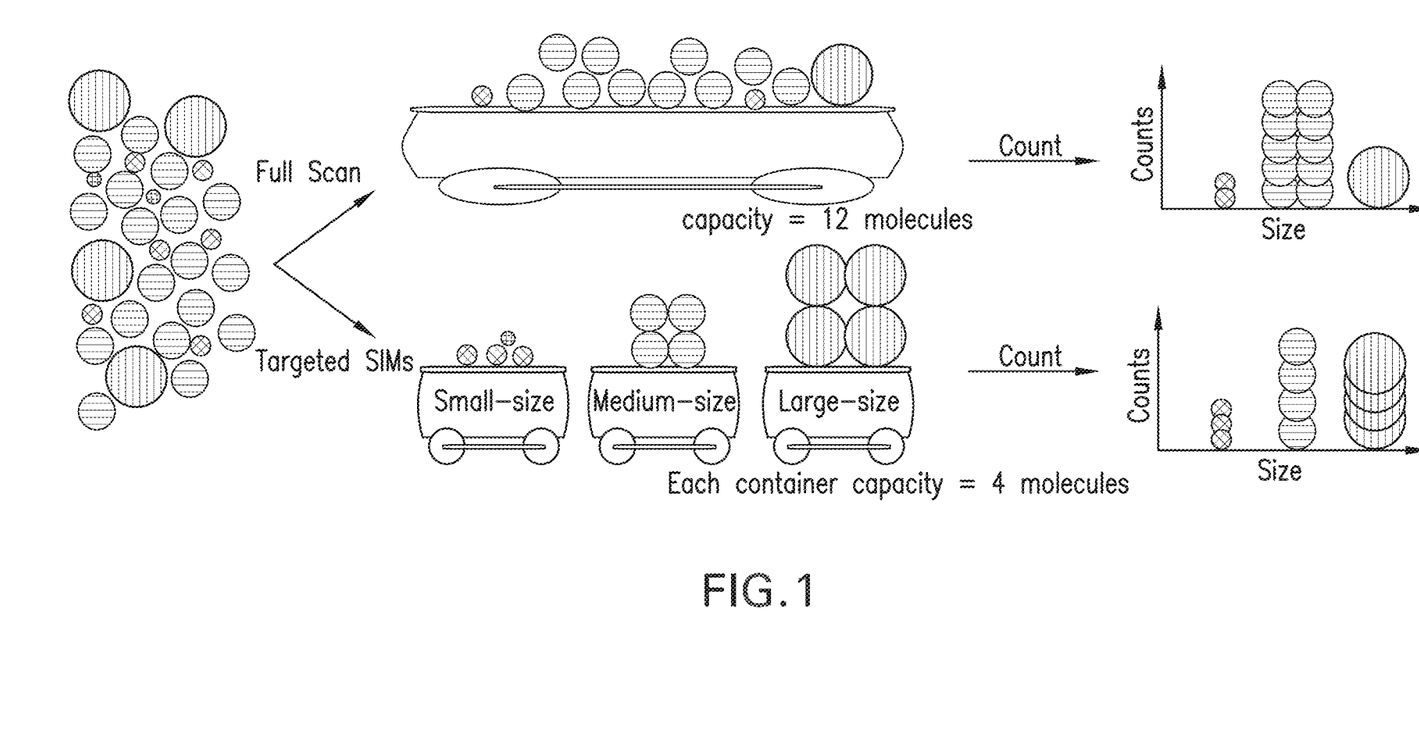
FIG. 1 shows a schematic illustrating two types of MS1 data acquisition: (1) Conventional full-scan MS1 acquisition and (2) Targeted SIM MS1 acquisition which is in accordance with embodiments disclosed herein. As shown, targeted SIM MS1 acquisition allows for lower abundance species to be detected.

Example 2: Multiplexed Targeted SIMs and Iterative MS2 DDA Acquisition Increase Robust Compound Identification for Cell Culture Medium Analysis Using the materials and methods described in Example 1, multiplexed targeted SIMs and iterative MS2 DDA acquisition was performed. FIG. 1 provides a schematic illustrating two types of MS1 data acquisition: (1) Conventional full-scan MS1 acquisition and (2) Targeted SIM MS1 acquisition which is in accordance with embodiments disclosed herein. Targeted SIM MS1 acquisition relies upon sorting molecules based upon size. By comparison, full scan MS1 detects a particular number of molecules regardless of size. As shown, targeted SIM MS1 acquisition allows for lower abundance species to be detected as only a particular number of each size of molecules is detected, thereby improving the confidence of detection. Targeted SIM MS1 included optimizing injection time and isolation windows.

Figure 3:
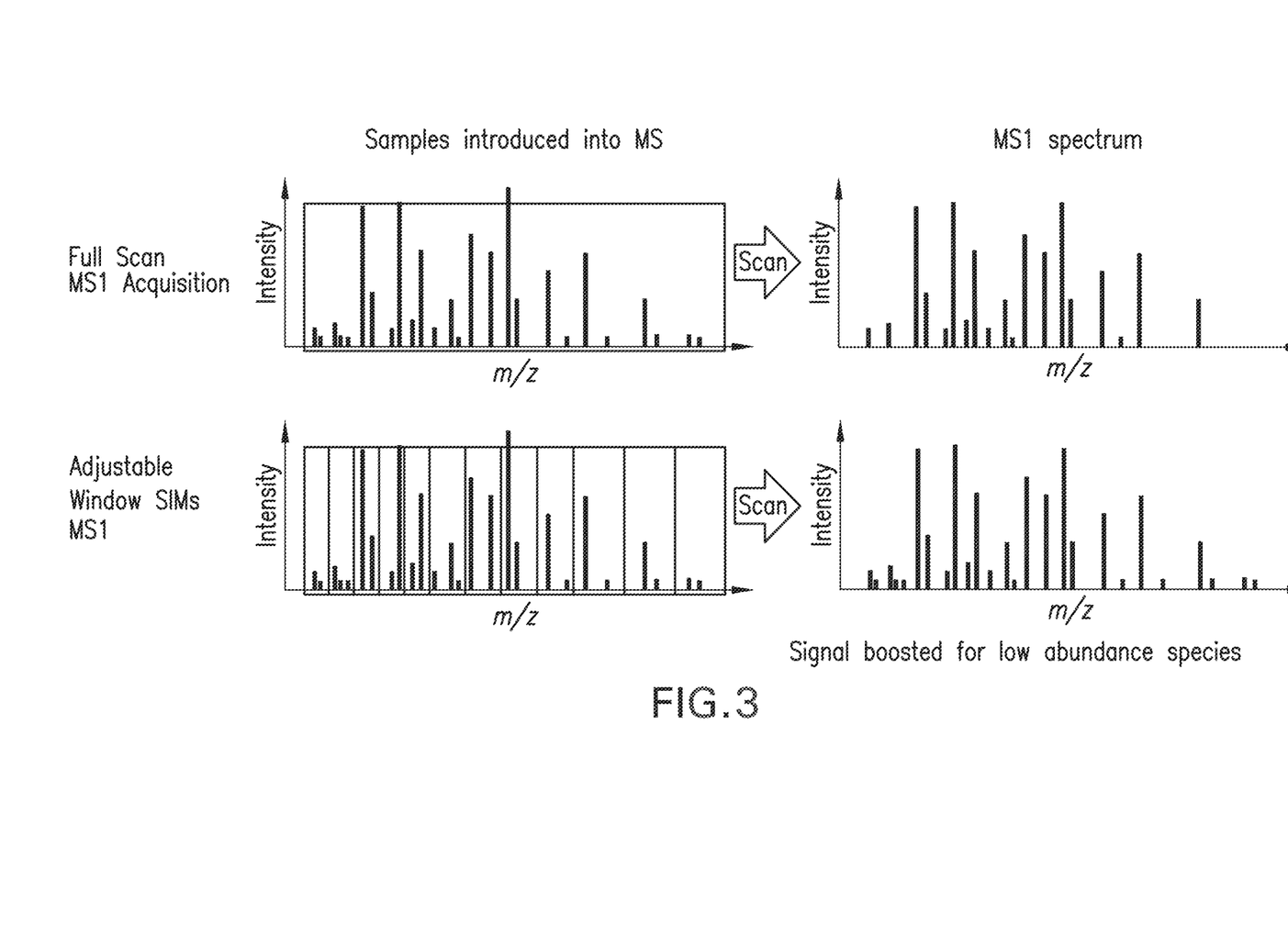
FIG. 3 shows MS1 spectra acquired following either conventional full scan MS1 acquisition (top tracing) or adjustable window SIMs MS1 acquisition in accordance with embodiments disclosed herein (bottom tracing).

In particular, FIG. 2 provides a schematic illustrating an exemplary adjustable window selection regimen which includes four segments ranging from 60 to 760.5 m/z: Segment 1, 60 m/z to 155.5 m/z with a window width of 10 Da; Segment 2, 155 m/z to 250.5 m/z, window width 10 Da; Segment 3, 250 m/z to 505.5 m/z, window width 25 DA; and Segment 4, 505.5 m/z to 760.5 m/z, window width 25 Da. Each segment included 10 windows and 0.5 Da overlap between adjacent windows. The width of the window varied between segments, however, it did not differ within a particular segment. Regions of particular interest had a smaller window width. FIG. 3 shows MS1 spectrums acquired following either conventional full scan MS1 acquisition (top tracing) or adjustable window SIMs MS1 acquisition in accordance with embodiments disclosed herein (bottom tracing). Comparing to MS1 full scan, multiplexed targeted SIMs provided cleaner background and higher intensity for several spiked-in stable isotope labeled compounds. For example, 10 nM of stable isotope labeled histidine was only observed by multiplexed targeted SIMs method.

Figure 4:
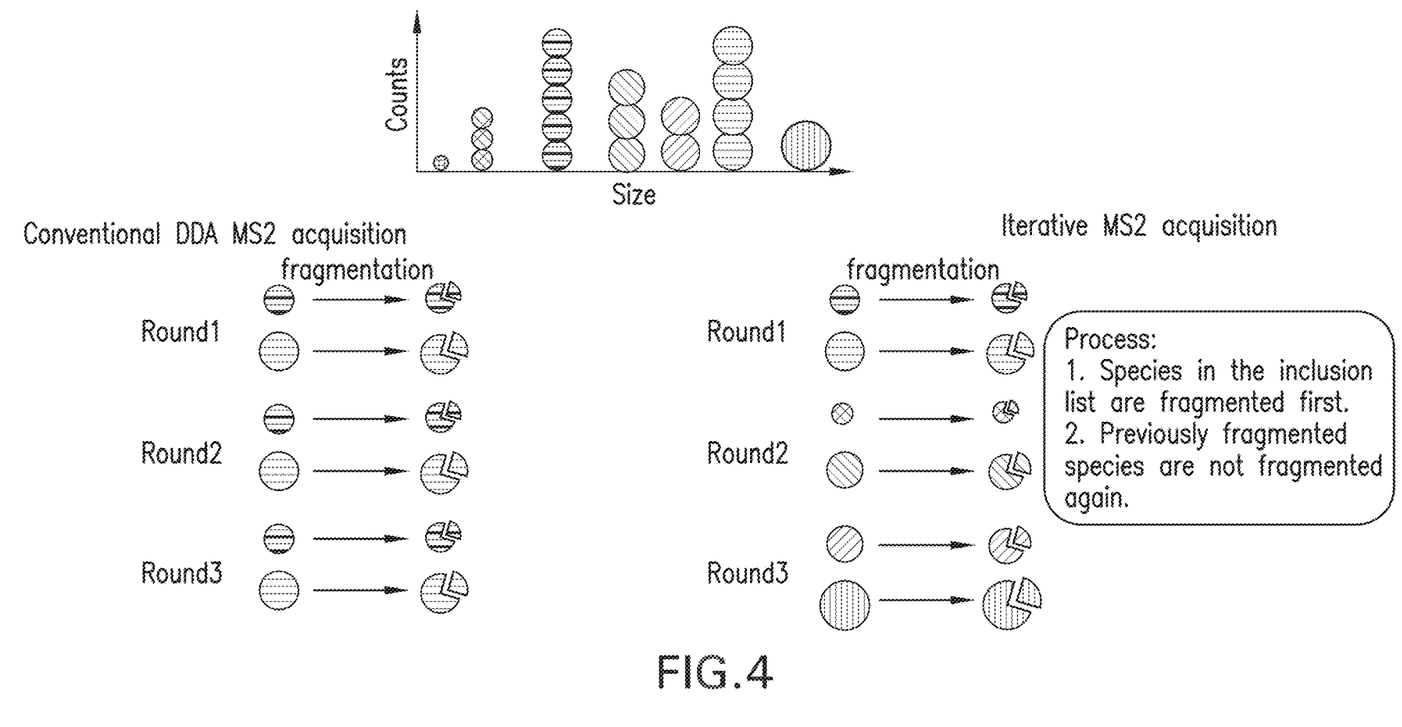
FIG. 4 shows a schematic illustrating two types of MS2 DDA: (1) Conventional DDA MS2 acquisition and (2) Iterative MS2 DDA platform acquisition in accordance with embodiments disclosed herein.

Following MS1 full scan or multiplexed targeted SIM, MS2 DDA was performed. FIG. 4 shows a schematic illustrating two types of MS2 DDA: (1) Conventional DDA MS2 acquisition and (2) Iterative DDA MS2 platform in accordance with embodiments disclosed herein.

Figure 5:
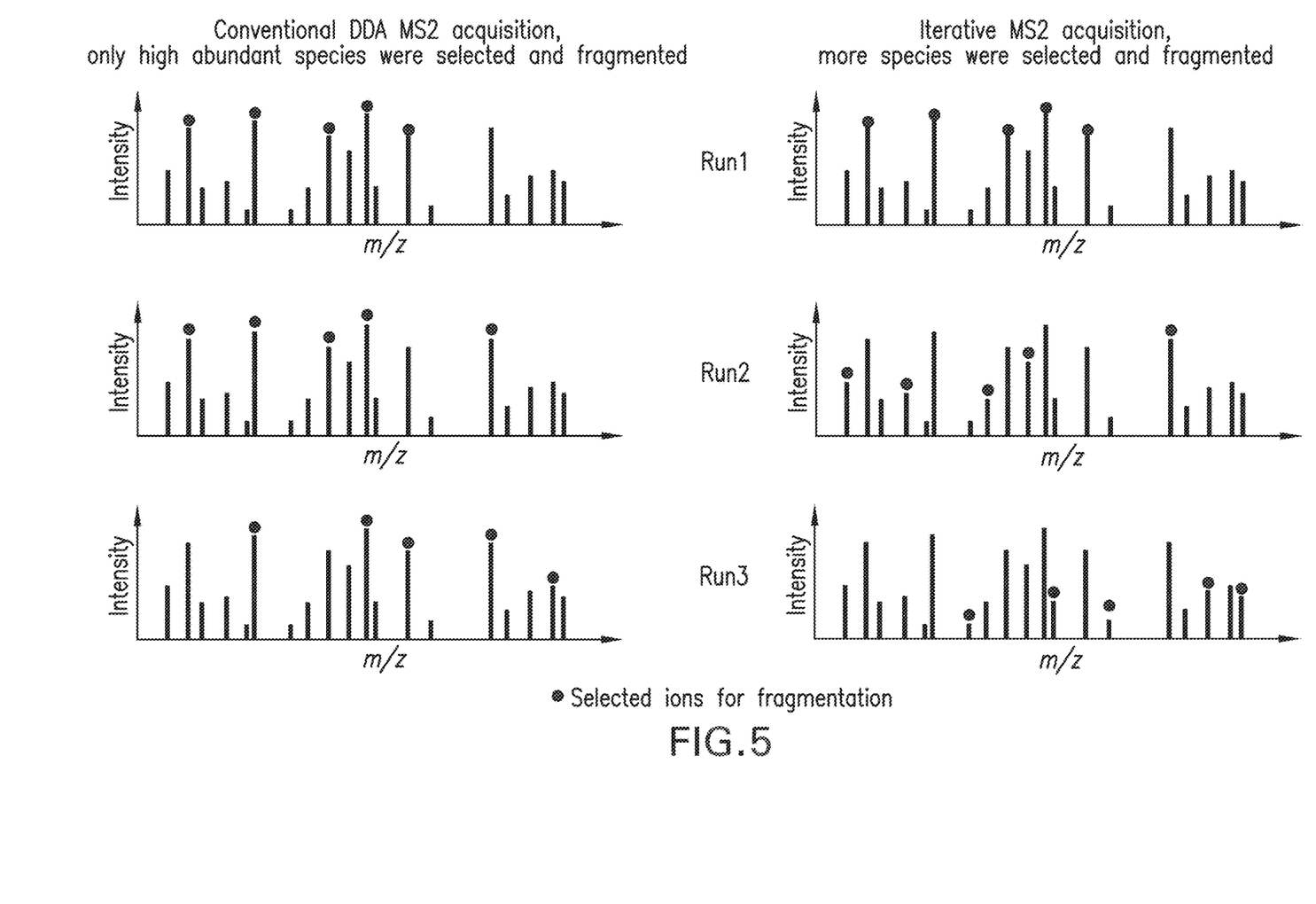
FIG. 5 shows iterative MS2 DDA results in more species being selected and fragmented in comparison with conventional MS2 DDA where only high abundant species were selected and fragmented.
Figure 6:
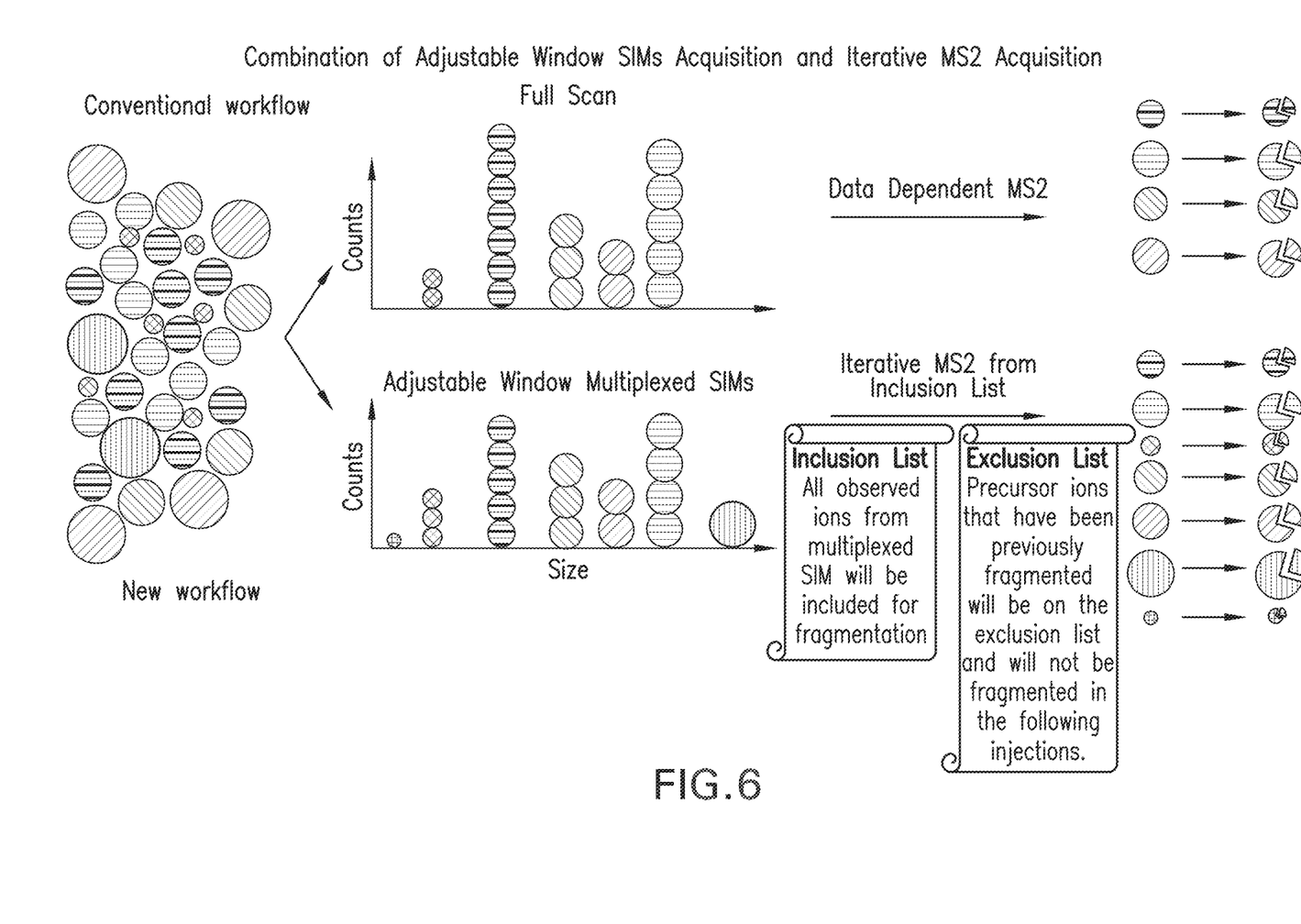
FIG. 6 shows a schematic comparing a conventional method of characterizing a sample and using a combination of adjustable window SIMs acquisition and iterative MS2 DDA in accordance with embodiments disclosed herein.
Figure 7:
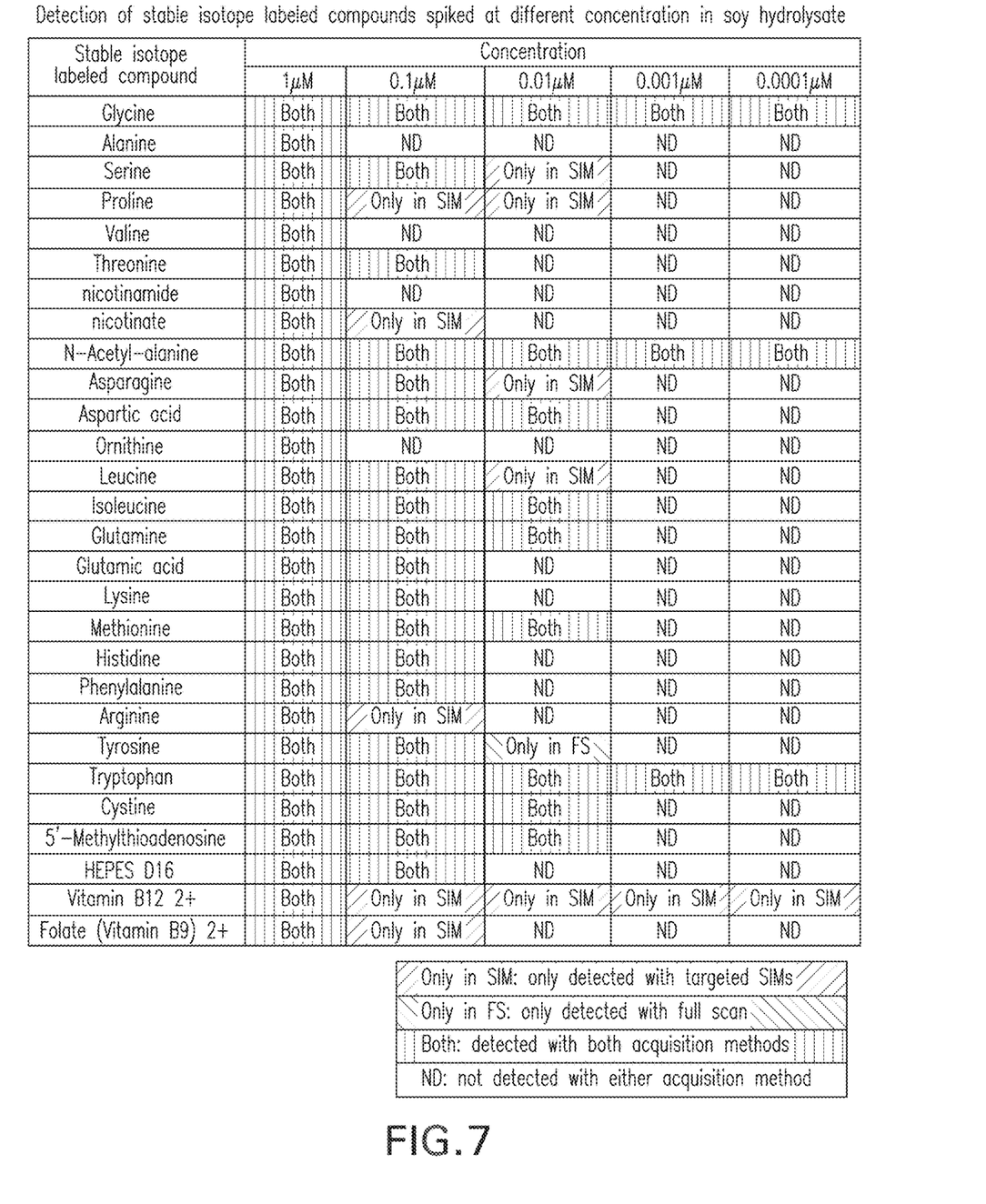
FIG. 7 shows a table illustrating the robustness and increased sensitivity of adjustable Window SIMs acquisition as compared to full scan MS. As the concentration of the compound decreased, the ability to detect the particular molecule was dependent upon the method utilized. Adjustable Window SIMs acquisition was capable of detecting molecules at lower concentrations than full scan MS.
Figure 8:
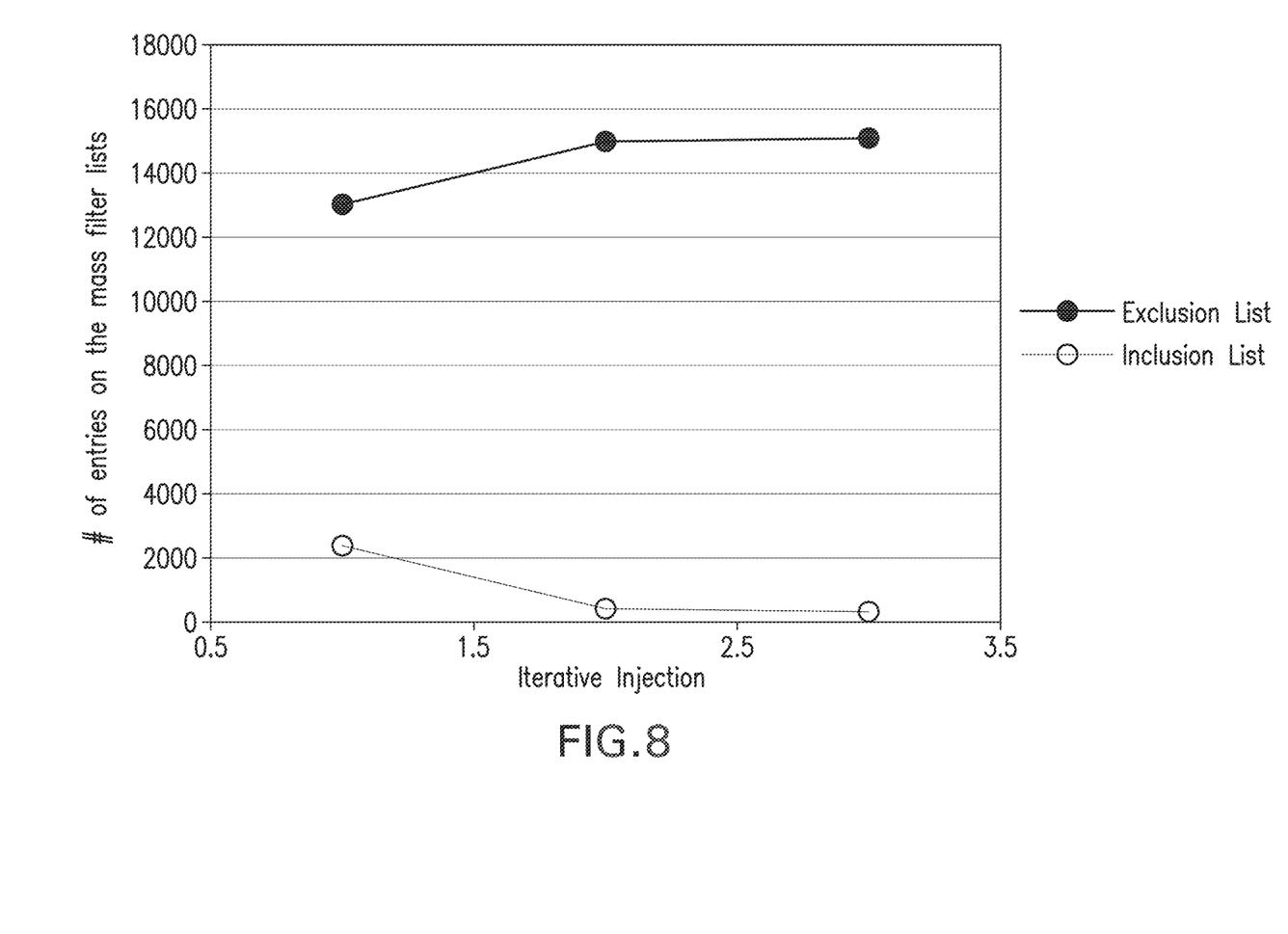
FIG. 8 shows a graph illustrating the strength of iterative MS2 DDA. The top line represents the number of entries on the mass filter exclusion list and bottom line is the number of entries on the mass filters inclusion list each in relation to iterative injection. As illustrated, as the iterative injection number increases, the exclusion list of species increases while the inclusion list decreases which in turn allows species of lower abundance to be fragmented and provide a robust, highly sensitive detection method.

FIG. 5 shows iterative MS2 data acquisition results in more species being selected and fragmented in comparison with conventional DDA MS2 acquisition where only high abundant species were selected and fragmented. FIG. 6 shows a schematic comparing a conventional method of characterizing a sample and using a combination of adjustable window SIMs acquisition and iterative MS2 acquisition in accordance with embodiments disclosed herein. As shown in FIG. 7, the combination of adjustable window SIMs acquisition and Iterative MS2 acquisition identified a variety of components with great complexity in soy hydrolysate samples, including amino acids, dipeptides, tripeptides, etc. with the abundance dynamic range of at least 4 orders of magnitude. FIG. 8 shows a graph illustrating the strength of iterative MS2 acquisition. The top line represents the number of entries on the mass filter exclusion list and bottom line is the number of entries on the mass filters inclusion list each in relation to iterative injection. As illustrated, as iterative injection increases, the exclusion list of species increases while the inclusion list decreases which in turn allows species of lower abundance to be detected. In the iterative MS2 DDA, the background ions in the blank run were successfully excluded during sample runs. With multiple iterative sample runs, MS2 scans were triggered on much lower abundant ions. Fast and high confidence component identification was achieved by searching against in-house library containing accurate mass, retention time and fragmentation spectra besides other online databases. It is contemplated that the disclosed method can be applied to analyze cell metabolites, such as for CHO cell metabolites analysis during cell culture development.

Overall, the disclosed methods provide a more robust, sensitive method for characterizing samples, such as cell culture medium and individual components and metabolites therein, which can be used to improve antibody process development.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. A method of characterizing a sample, comprising:
providing the sample to a liquid chromatography system capable of sample separation to generate sample components;
analyzing sample components by multiplexed targeted selected ion monitoring (SIM) to select a plurality of precursor ions, wherein analyzing sample components by multiplexed SIM to select a plurality of precursor ions comprises segments of mass-to-charge ratios (m/z), wherein each segment comprises multiple windows, wherein the windows overlap; and
performing iterative mass spectral data-dependent acquisition (DDA) on the plurality of precursor ions, wherein preforming iterative mass spectral DDA comprises utilizing an iterative inclusion list and an iterative exclusion list, wherein the iterative exclusion list comprises a precursor ion that has been previously fragmented from the plurality of precursor ions.

2. The method of claim 1, wherein the liquid chromatography system is a reversed phase liquid chromatography (RPLC) system, an ion-exchange chromatography system, a size exclusion chromatography system, an affinity chromatography system, a hydrophilic-interaction chromatography system, or a hydrophobic chromatography system.

3. The method of claim 1, wherein analyzing sample components by multiplexed targeted selected ion monitoring (SIM) to select a plurality of precursor ions comprises utilizing an ion trap or orbitrap mass analyzer.

4. The method of claim 1, wherein performing iterative mass spectral DDA comprises utilizing an ion trap or orbitrap mass analyzer fitted with a segmented quadrupole mass filter.

5. The method of claim 1, wherein the sample is a cell culture medium.

6. The method of claim 5, wherein the cell culture medium is for a recombinant cell-based production system.

7. The method of claim 6, wherein the recombinant cell-based production system is a mammalian system.

8. The method of claim 6, wherein the recombinant cell-based production system is for production of a protein.

9. The method of claim 8, wherein the protein is an antibody, a fusion protein, recombinant protein, or a combination thereof.

10. The method of claim 9, wherein the antibody is of isotype IgG1, IgG2, IgG3, IgG4, or mixed isotype.

11. A method of identifying a compound in a sample of a cell culture medium, comprising:
    providing the sample of the cell culture medium to a liquid chromatography system capable of sample separation to generate sample components;
    analyzing sample components by multiplexed targeted selected ion monitoring (SIM) to select a plurality of precursor ions, wherein analyzing sample components by multiplexed SIM to select a plurality of precursor ions comprises segments of mass-to-charge ratios (m/z), wherein each segment comprises multiple windows, wherein the windows overlap; and
    performing iterative mass spectral data-dependent acquisition (DDA) on the plurality of precursor ions, wherein preforming iterative mass spectral DDA comprises utilizing an iterative inclusion list and an iterative exclusion list, wherein the iterative exclusion list comprises a precursor ion that has been previously fragmented from the plurality of precursor ions.

12. The method of claim 11, wherein the liquid chromatography system is a reversed phase liquid chromatography (RPLC) system, an ion-exchange chromatography system, a size exclusion chromatography system, an affinity chromatography system, a hydrophilic-interaction chromatography system, or a hydrophobic chromatography system.

13. The method of claim 11, wherein analyzing sample components by multiplexed targeted selected ion monitoring (SIM) to generate an inclusion list comprises utilizing an ion trap or orbitrap mass analyzer.

14. The method of claim 11, wherein performing iterative mass spectral DDA comprises utilizing an ion trap or orbitrap mass analyzer fitted with a segmented quadrupole mass filter.

15. The method of claim 11, wherein the cell culture medium is a soy-based cell culture medium.

16. The method of claim 11, wherein the cell culture medium is for a recombinant cell-based production system.

17. The method of claim 16, wherein the recombinant cell-based production system is a mammalian system.

18. The method of claim 16, wherein the recombinant cell-based production system is for production of a protein.

19. The method of claim 18, wherein the protein is an antibody, a monoclonal antibody, a fusion protein, recombinant protein, or a combination thereof.

20. The method of claim 19, wherein the monoclonal antibody is of isotype IgG1, IgG2, IgG3, IgG4, or mixed isotype.

* * * * *